US012336767B2

(12) United States Patent
Govari et al.

(10) Patent No.: US 12,336,767 B2
(45) Date of Patent: Jun. 24, 2025

(54) FINDING ROLL ANGLE OF DISTAL END OF DEFLECTABLE OR NON-DEFLECTABLE INVASIVE MEDICAL INSTRUMENT

(71) Applicant: BIOSENSE WEBSTER (ISRAEL) LTD., Yokneam (IL)

(72) Inventors: Assaf Govari, Haifa (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 509 days.

(21) Appl. No.: 16/812,928

(22) Filed: Mar. 9, 2020

(65) Prior Publication Data

US 2021/0275255 A1 Sep. 9, 2021

(51) Int. Cl.

| | |
|---|---|
| ***A61B 34/20*** | (2016.01) |
| ***A61B 17/24*** | (2006.01) |
| ***A61B 17/32*** | (2006.01) |
| ***A61B 90/00*** | (2016.01) |
| *A61B 17/00* | (2006.01) |

(52) U.S. Cl.

CPC .............. *A61B 34/20* (2016.02); *A61B 17/24* (2013.01); *A61B 17/320016* (2013.01); *A61B 90/37* (2016.02); *A61B 2017/00738* (2013.01); *A61B 2034/2051* (2016.02); *A61B 2217/005* (2013.01)

(58) Field of Classification Search

CPC ............ A61B 17/24; A61B 17/320016; A61B 2017/00738; A61B 34/20; A61B 2034/2046; A61B 2034/2051; A61B 2034/2053

See application file for complete search history.

(56) References Cited

U.S. PATENT DOCUMENTS

| | | | | |
|---|---|---|---|---|
| 5,676,673 | A | 10/1997 | Ferre et al. | |
| 6,272,371 | B1 | 8/2001 | Shlomo | |
| 9,980,786 | B2 | 5/2018 | Saul et al. | |
| 2005/0154255 | A1* | 7/2005 | Jacobs | A61B 17/32002 600/104 |
| 2006/0089633 | A1 | 4/2006 | Bleich et al. | |
| 2007/0080682 | A1 | 4/2007 | Govari | |

(Continued)

FOREIGN PATENT DOCUMENTS

| | | | |
|---|---|---|---|
| CN | 206434358 | 8/2017 | |
| WO | WO-2014058838 A1 * | 4/2014 | A61B 1/0005 |

OTHER PUBLICATIONS

U.S. Appl. No. 16/375,485, filed Apr. 4, 2019.
International Search Report mailed Jun. 4, 2021 from corresponding PCT Patent Application No. PCT/IB2021/051758.

*Primary Examiner* — Diane D Yabut
*Assistant Examiner* — Christian D Knauss
(74) *Attorney, Agent, or Firm* — Frost Brown Todd LLP

(57) ABSTRACT

A system includes a medical instrument, a position sensor, and a processor. The medical instrument includes a handle and a head, the head being configured for insertion into an organ of a patient and having a feature that is rotationally-asymmetric about a longitudinal axis of the medical instrument. The position sensor, which is disposed on the head and is configured to generate signals in response to an externally-applied magnetic field. The processor is configured to receive the signals generated by the position sensor on the head, and estimate, based on the received signals, a roll angle of the rotationally-asymmetric feature of the head.

19 Claims, 4 Drawing Sheets

(56) References Cited

U.S. PATENT DOCUMENTS

| | | | | |
|---|---|---|---|---|
| 2011/0098708 | A9 | 4/2011 | Saadat et al. | |
| 2014/0275810 | A1* | 9/2014 | Keller | A61B 5/065 600/300 |
| 2016/0007842 | A1 | 1/2016 | Govari et al. | |
| 2016/0008083 | A1* | 1/2016 | Kesten | A61B 5/062 600/424 |
| 2017/0007156 | A1* | 1/2017 | Govari | A61B 5/062 |
| 2018/0070928 | A1 | 3/2018 | Jones et al. | |
| 2018/0280049 | A1 | 10/2018 | Algawi et al. | |
| 2018/0333165 | A1* | 11/2018 | Algawi | A61B 17/24 |
| 2018/0353102 | A1* | 12/2018 | Govari | A61B 90/37 |
| 2019/0015127 | A1* | 1/2019 | Cheng | A61B 34/20 |
| 2019/0069959 | A1 | 3/2019 | Palushi et al. | |
| 2019/0314089 | A1* | 10/2019 | Shameli | A61B 17/320708 |
| 2019/0388156 | A1 | 12/2019 | Shameli | |
| 2020/0069218 | A1 | 3/2020 | Gliner et al. | |
| 2020/0107885 | A1* | 4/2020 | Palushi | A61B 34/20 |

* cited by examiner

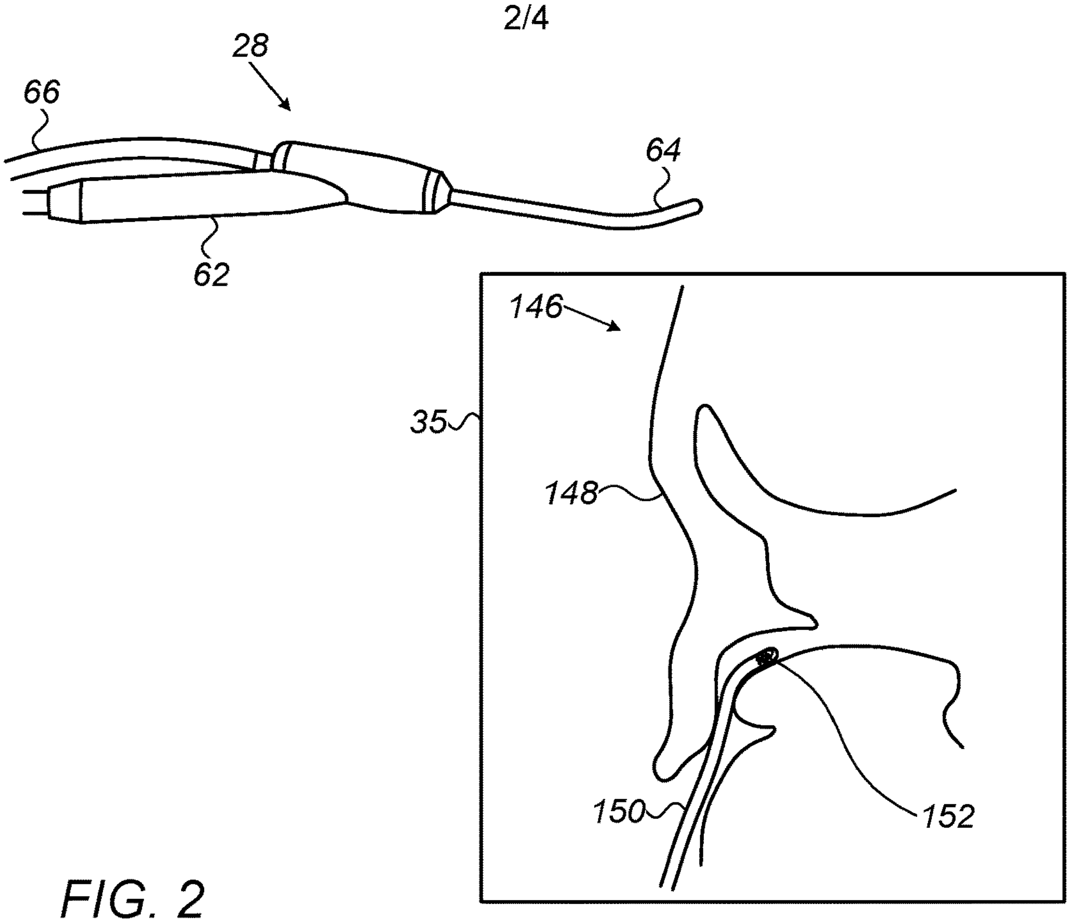
FIG. 2
FIG. 3
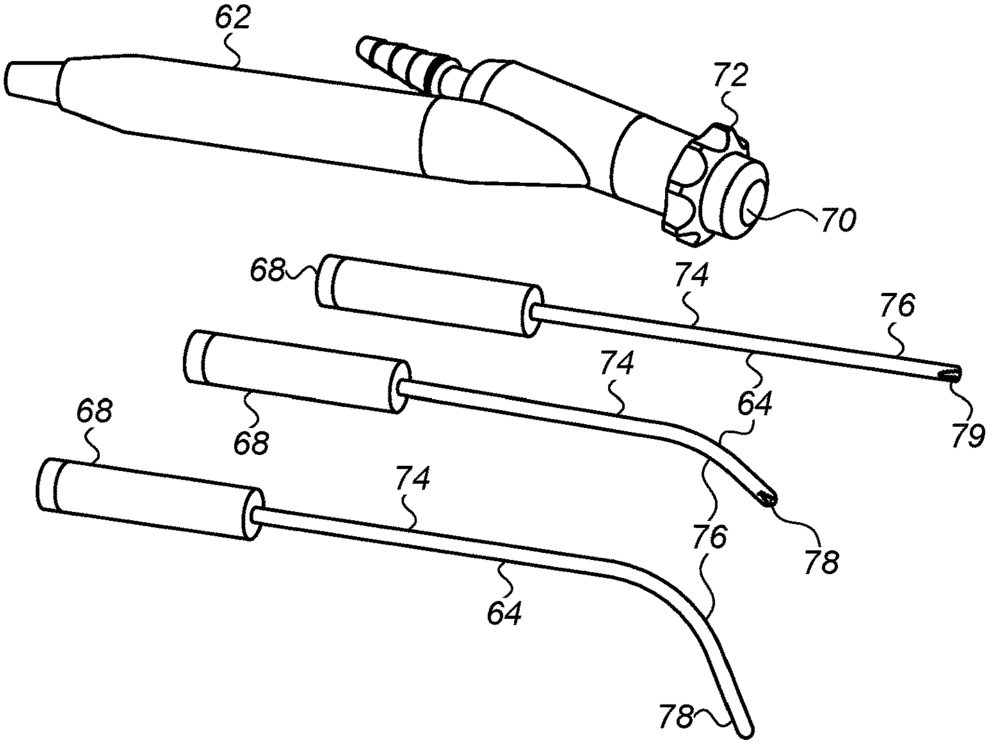

FINDING ROLL ANGLE OF DISTAL END OF DEFLECTABLE OR NON-DEFLECTABLE INVASIVE MEDICAL INSTRUMENT

FIELD OF THE INVENTION

The present invention relates in general to medical instruments, and in particular to the tracking of an invasive instrument inside an organ of a patient.

BACKGROUND

Techniques for tracking a medical instrument in an organ of a patient were previously reported in the patent literature. For example, U.S. Patent Application Publication 2018/0280049, issued as U.S. Pat. No. 10,537,350 on Jan. 21, 2020, describes a medical device that includes a disposable Ear-Nose-Throat (ENT) tool, a reusable handle, and a processor. The ENT tool is configured to perform a medical procedure in a patient ENT organ. The reusable handle is configured to hold and control the disposable ENT tool, and includes a position sensor configured to produce one or more position signals that are indicative of a first position of the reusable handle. The processor is configured to receive the position signals from the position sensor, and to estimate, based on the position signals, a second position of the disposable ENT tool in the patient ENT organ.

As another example, U.S. Pat. No. 6,272,371 describes an invasive probe apparatus including flexible elongate probe having a distal portion adjacent to a distal end thereof for insertion into the body of a subject. The distal portion assumes a predetermined curve form when a force is applied thereto. First and second sensors are fixed to the distal portion of the probe in known positions relative to the distal end, which sensors generate signals responsive to bending of the probe. Signal processing circuitry receives the bend responsive signals and processes them to find position and orientation coordinates of at least the first sensor, and to determine the locations of a plurality of points along the length of the distal portion of the probe.

SUMMARY

An embodiment of the present invention provides a system including a medical instrument, a position sensor, and a processor. The medical instrument includes a handle and a head, the head being configured for insertion into an organ of a patient and having a feature that is rotationally-asymmetric about a longitudinal axis of the medical instrument. The position sensor, which is disposed on the head and is configured to generate signals in response to an externally-applied magnetic field. The processor is configured to receive the signals generated by the position sensor on the head, and estimate, based on the received signals, a roll angle of the rotationally-asymmetric feature of the head.

In some embodiments, the position sensor includes at least a coil having an axis oriented at a given rotational angle relative to the rotationally-asymmetric feature of the head.

In some embodiments, the rotationally-asymmetric feature includes a medical tool.

In an embodiment, the medical tool includes an ear, nose and throat (ENT) shaver. In another embodiment, the medical tool includes an ENT suction tool. In yet another embodiment, the medical tool includes an ENT microbrider. In a further embodiment, the rotationally-asymmetric feature includes an opening of the medical tool. In an additional embodiment, the medical tool is bent with respect to the longitudinal axis.

In some embodiments, the position sensor is a single axis sensor (SAS) printed on a circuit board.

In some embodiments, the position sensor is a dual axis sensor (DAS) printed on a circuit board.

In an embodiment, the system further includes a location pad, which includes at least one magnetic field radiator configured to transmit the magnetic fields in a vicinity of the organ.

In another embodiment, the system further includes a display, wherein the processor is configured to (a) track a location of the head responsively to the received signals, and (b) render to the display an image including a representation of at least part of the organ and a representation of at least part of the head in the body.

There is additionally provided, in accordance with another embodiment of the present invention, a method including inserting into an organ of a patient a medical instrument including a handle and a head, the head having a feature that is rotationally-asymmetric about a longitudinal axis of the medical instrument. Using a position sensor disposed on the head, signals are generated in response to an externally-applied magnetic field. The signals generated by the position sensor on the head are received and, based on the received signals, a roll angle of the rotationally-asymmetric feature of the head is estimated.

The present invention will be more fully understood from the following detailed description of the embodiments thereof, taken together with the drawings in which:

BRIEF DESCRIPTION OF THE DRAWINGS

FIG. 2 is a schematic view of the ear-nose-throat (ENT) instruments used in FIG. 1, and of a representation of sinuses with an inserted interchangeable head of the ENT instrument, according to an embodiment of the present invention;

FIG. 3 is a schematic view of a handle and interchangeable heads of the ear-nose-throat (ENT) instruments of FIG. 2, according to an embodiment of the present invention;

DETAILED DESCRIPTION OF EMBODIMENTS

Overview

Figure 1:
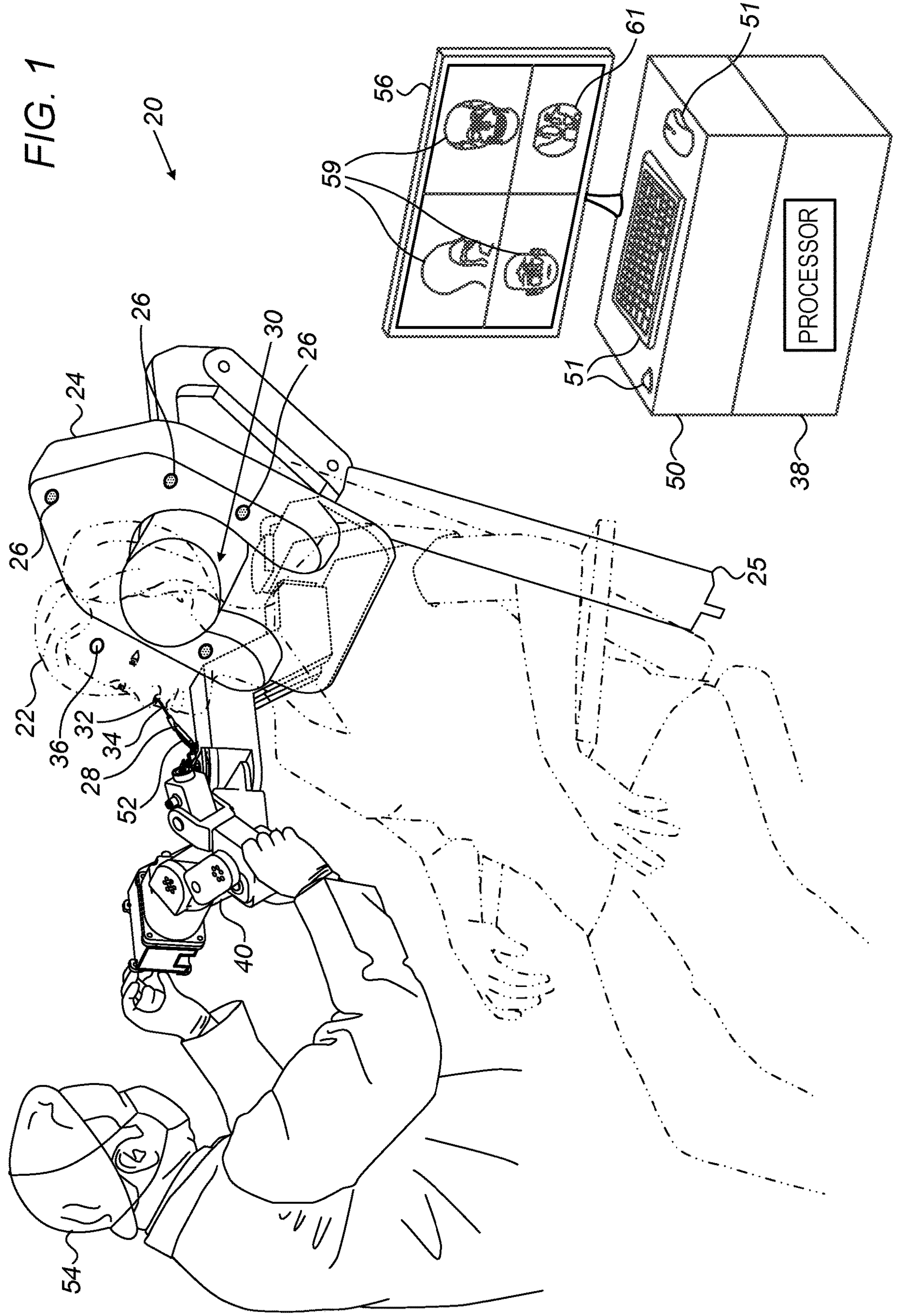
FIG. 1 is a schematic, pictorial illustration of an ear-nose-throat (ENT) instrument tracking system, according to an embodiment of the present invention.

Some invasive medical procedures may require tracking a rotational orientation of a distal end of medical instrument inside an organ of a patient. The medical instrument may include a handle with multiple interchangeable heads that may be rigid and straight, rigid with a curved portion (e.g., a curved distal edge), or with a deflectable distal edge. Furthermore, even straight heads may include features or components that are rotationally-asymmetric. The rotationally asymmetrically shaped interchangeable heads, e.g., such as those including a tool disposed at a preferred rotational orientation with respect to the head, are so configured to perform different therapeutic functions and/or to access different organs, including cavities. Therefore, to be used inside an organ, e.g., for cutting tissue, a physician must know the rotational orientation of the tool relative to a target tissue of the organ.

Furthermore, some of the medical instruments may allow an interchangeable rigid head to be inserted into the handle in one of multiple rotational positions. Additionally or alternatively, some medical instruments may allow the inserted head to be rotated to multiple positions. These options may further increase the physician's uncertainty as to an actual rotational orientation of the tool, e.g., of a cutting tool, relative to target tissue.

As another example, rigid heads of ear-nose-throat (ENT) instruments may include, at their distal end, a rotationally asymmetrically aligned electrical cutting element, such as a partially covered rotating blade or rotating bur, that is disposed on the head at a given rotational orientation and used to remove tissue inside the nasal sinuses of a patient. Again, to perform this task, the physician must know how to accurately rotate the head of the electrical cutting element so it faces target tissue.

Embodiments of the present invention that are described hereinafter enable accurate tracking of a roll angle of a rotationally-asymmetric feature, such as a tool, about a longitudinal axis of a head of a medical instrument inside an organ. The disclosed techniques enable a physician to accurately operate a tool disposed at a distal end of the head in treatment of a target tissue (e.g., to accurately operate an ENT shaver or ENT suction device inside the sinuses of a patient). The head of the medical instrument may be interchangeable or fixed.

The disclosed embodiments provide a position sensor, such as a magnetic position sensor, coupled to the instrument head which is capable of indicating, in response to an externally-applied magnetic field, to a user, the rotational orientation (i.e., a roll angle) of the head to indicate a rotational orientation of a component of the head. Examples of a component include the aforementioned cutting tool, or, as another example, a bent distal edge comprising an irrigation port.

In some embodiments, using a magnetic tracking system, a processor uses signals from the magnetic sensor to determine the roll angle of the distal end.

In one embodiment, the disclosed magnetic sensor is a single axis sensor (SAS) with the axis of its coil aligned at a given rotational angle relative to a rotational orientation the feature (e.g., of a cutting tool), to track the roll angle of the feature (e.g., the cutting tool) inside the organ, e.g., relative to a rendered anatomy.

In another embodiment, the sensor is a dual-axis sensor (DAS), comprising, for example, two orthogonal wound coils which may track a position, direction, and roll angle of the respective feature. The DAS has an axis of one of its coils aligned at a given rotational angle relative to a rotational orientation the feature.

The SAS or DAS may be printed on a printed circuit board (PCB) for attaching to the head.

As indicated above, using a SAS, an image including a representation of at least part of an organ, and a representation of the distal end of the inserted interchangeable head of the medical instrument in the organ, may be rendered on a display responsively to the tracked roll angle of the distal end of the inserted interchangeable head. Using a DAS, the representation may be rendered on a display responsively to the tracked position, direction, and roll angle of the distal end of the inserted interchangeable head.

By providing exact rotational information of a distal end, a feature (e.g., a rotationally asymmetrically shaped distal suction-aperture, or a tool such as a blade) disposed at a given rotational orientation at the distal end can be used more effectively and safely in invasive procedures.

System Description

FIG. 1 is a schematic, pictorial illustration of an ear-nose-throat (ENT) instrument tracking system 20, according to an embodiment of the present invention. Medical procedures for which system 20 is typically used include invasive and/or investigative procedures on nasal sinuses and on other ENT tissue that can be accessed via the nasal cavity, such as an adenoid or the eustachian canal. However, the system, mutatis mutandis, can be further used to treat other body organs (such as the brain) of a patient 22.

In the shown embodiment, a magnetic field radiation assembly 24 is positioned behind and/or around the head of patient 22, for example by fixing the assembly 24 to a chair 25 (or bed) upon which the patient is sitting (or lying). The magnetic field radiation assembly 24 in the pictured example comprises five magnetic field radiators 26, which are fixed in a horseshoe shaped frame, the frame being positioned beneath or around the head of patient 22 so that the magnetic field radiators 26 surround the head of patient 22. Alternatively, smaller or larger numbers of radiators 26 may be used in various different configurations. The magnetic field radiators 26 are configured to radiate alternating magnetic fields at respective frequencies into a region 30 where the head of patient 22 is located.

The alternating magnetic fields induce signals in a magnetic position sensor 32 and a magnetic position sensor 36. Position sensor 32 is shown disposed on an ENT instrument 28 in order to track a position, direction, and roll angle of a distal end 34 of ENT instrument 28. Position sensor 36 is shown disposed on patient 22 (e.g., on the forehead of patient 22) in order to track a position of the head of patient 22 and to compensate for movement of the patient's head with respect to the magnetic field radiation assembly 24. By way of example only, ENT instrument 28 may include any one or more of the following: a suction tool, microdebrider, or a shaver.

Distal end 34 of the ENT instrument 28 and the head of patient 22 are tracked using a tracking subsystem running on a processor 38. Position sensor 32 includes at least one coil, described in more detail in FIG. 4. To determine a roll angle of distal end 34 of ENT instrument 28 inside the sinuses of patient 22, position sensor 32 is affixed to ENT instrument 28 with an axis of at least one coil of sensor 32 being disposed at a given rotational orientation relative to a physical feature or component of the distal end (e.g., a cutting tool disposed over the distal end) whose roll angle is to be tracked, as described above.

A system using magnetic field radiators for tracking an entity inserted into a patient, such as the magnetic field radiators 26, is described in U.S. Patent Application Publication 2016/0007842, issued as U.S. Pat. No. 10,772,489 on Sep. 15, 2020, which is incorporated herein by reference. In addition, the Carto® system produced by Biosense Webster, Irvine, California, uses a tracking system similar to that described herein for finding the location and orientation of a coil in a region irradiated by magnetic fields.

In some embodiments, medical instrument 28 is attached to, and held by, a robotic arm 40, which includes a plurality of robotic joints configured to control movement of robotic arm 40 and to manipulate ENT instrument 28. In other embodiments, ENT instrument 28 is held and manipulated by physician 54. The robotic arm 40 generally has its own robotic coordinate system. The robotic coordinate system is registered with a magnetic coordinate system of the magnetic field radiators 26, or vice-versa. Registration of the robotic coordinate system with the magnetic coordinate system may be performed, for example, by moving the robotic arm 40, or ENT instrument 28 attached to the robotic arm 40, to one or more locations known to the magnetic field radiators 26, for example, to a location on the magnetic field radiation assembly 24. Once registration of the robotic coordinate system with the magnetic coordinate system has been performed, locations in the magnetic coordinate system can be translated to the robotic coordinate system in order to correctly manipulate robotic arm 40.

Processor 38 comprises a processing unit communicating with one or more memories. Typically, the elements may be connected by cables to processor 38. Alternatively or additionally, the elements may be coupled wirelessly to processor 38. Processor 38 may be mounted in a console 50, which comprises operating controls 51 that typically include a keypad and/or a pointing device such as a mouse or trackball. The console 50 also connects to other elements of system 20, such as a proximal end 52 of ENT instrument 28. A physician 54 uses the operating controls 51 to interact with processor 38 while performing the procedure, and processor 38 may present results produced by system 20 on a display 56.

In some embodiments, prior to performing the medical procedure, CT images of the patient 22 are acquired. The CT images are stored in a memory (not shown) for subsequent retrieval by processor 38. In FIG. 1, display 56 displays various views 59 of a previous CT scan (or other suitable scan) which may be used as an aid for physician 54 to guide ENT instrument 28 inside the sinuses. The display screen 56 also shows an image 61 captured by a camera (not shown) of ENT instrument 28. The CT images may be registered with the magnetic coordinate system so that a representation of the ENT instrument 28 may be displayed with the CT images on the display 56, as will be described in more detail in FIG. 2.

In practice, some or all of these functions of processor 38 may be combined in a single physical component or, alternatively, implemented using multiple physical components. These physical components may comprise hard-wired or programmable devices, or a combination of the two. In some embodiments, at least some of the functions of the processor may be carried out by a programmable processor under the control of suitable software. This software may be downloaded to a device in electronic form, over a network, for example. Alternatively or additionally, the software may be stored in tangible, non-transitory computer-readable storage media, such as optical, magnetic, or electronic memory.

Finding Roll Angle of Distal End of Deflectable or Non-Deflectable Invasive Medical Instrument FIG. 2 is a schematic view of the ear-nose-throat (ENT) instrument 28 used in FIG. 1, and of a representation of sinuses with an inserted interchangeable head 64 of ENT instrument 28, according to an embodiment of the present invention. ENT instrument 28 includes a handle 62 in which a plurality of different rigid interchangeable heads 64 are individually reversibly insertable. FIG. 2 shows one of the interchangeable heads 64 inserted into handle 62. Other examples of interchangeable heads 64 are shown in FIG. 3, which is described below. ENT instrument 28 shown in FIG. 2 also includes an irrigation or drainage tube 66.

ENT instrument 28 is shown in FIG. 2 prior to a position sensor being added to the ENT tool. In fact, in some embodiments, ENT instrument 28 may be implemented with an off-the-shelf medical instrument which is sold without a position sensor and to which a position sensor is added at an appropriate position, as will be described in FIG. 4. For example, the Bien Air® S120 hand-piece and interchangeable reusable blades, available without a position sensor, may be adapted to provide the ENT instrument 28 described hereinbelow. In other embodiments, ENT instrument 28 may be implemented as a purpose-built medical instrument with integral position sensors.

Inset 35 of FIG. 2 shows a schematic view of an image 146 of a representation 148 of the nasal sinuses and of a representation 150 of an inserted interchangeable head 64 rendered by processor 38 system 20 of FIG. 1. Processor 38 is configured to render image 146 on display 56 (FIG. 1) including the representation 148 of at least part of the sinuses and representation 150 of at least part of the inserted interchangeable head 64 of ENT instrument 28 in the sinuses responsively to the tracked location, direction, and roll angle of the distal end of interchangeable head 64. As the interchangeable heads 64 are rigid, the representation 150 of the inserted interchangeable head 64 may be rendered based on the coordinates of a single point of the inserted interchangeable head 64 and a known shape of the identified inserted interchangeable head 64. A treatment tool, such as a cutting element 78, may also be indicated using an indicator 152 on the representation 150.

FIG. 3 is a schematic view of handle 62 and interchangeable heads 64 of ear-nose-throat (ENT) instrument 28 of FIG. 2, according to an embodiment of the present invention. Interchangeable heads 64 are shown in FIG. 3 without a position sensor. Interchangeable heads 64 are different from each other with respect to a head shape and functionality.

Each interchangeable head 64 includes a plastic proximal end 68 which is inserted into a socket 70 of handle 62. Socket 70 of handle 62 includes multiple rotational positions in which to insert the different rigid interchangeable heads 64. For example, with the S120 hand-piece, the reusable blades may be inserted in eight different rotational positions. In some embodiments, interchangeable heads 64 may be inserted into the socket 70 only in a single rotational position.

Handle 62 includes multiple rotational positions to rotate the different rigid interchangeable heads 64. Therefore, once one of the interchangeable heads 64 has been inserted into socket 70, the inserted interchangeable head 64 may be rotated to multiple rotational positions using a rotational adjustment cog wheel 72. In other embodiments, the inserted interchangeable head 64 cannot be rotated to another position.

In the example of FIG. 3, each of the interchangeable heads 64 is implemented with an elongated shaft 74 having a distal end 76, which includes at least one cutting element 78 or a distal opening 79 at the distal end 76 of the elongated shaft 74, opening 79 being shaped asymmetrically in terms of its rotation. Distal opening 79 may be used, for example, to expose a shaver only over a given range of azimuthal angles to prevent collateral damage to surrounding tissue after the tool is rotated to face a target tissue. The cutting element(s) 78 may include a shaving bur (e.g., a cylindricalor ball-shape element with a rough surface), a rotating shaving blade inside the elongated shaft 74, or any other suitable cutting element.

Further aspects of ENT instruments of the kinds described above can be found in U.S. patent application Ser. No. 16/375,485, entitled, "Medical Instrument Identification," filed Apr. 4, 2019, issued as U.S. Pat. No. 11,298,207 on Apr. 12, 2022, which is assigned to the assignee of the present patent application and whose disclosure is incorporated herein by reference.

Figure 4:
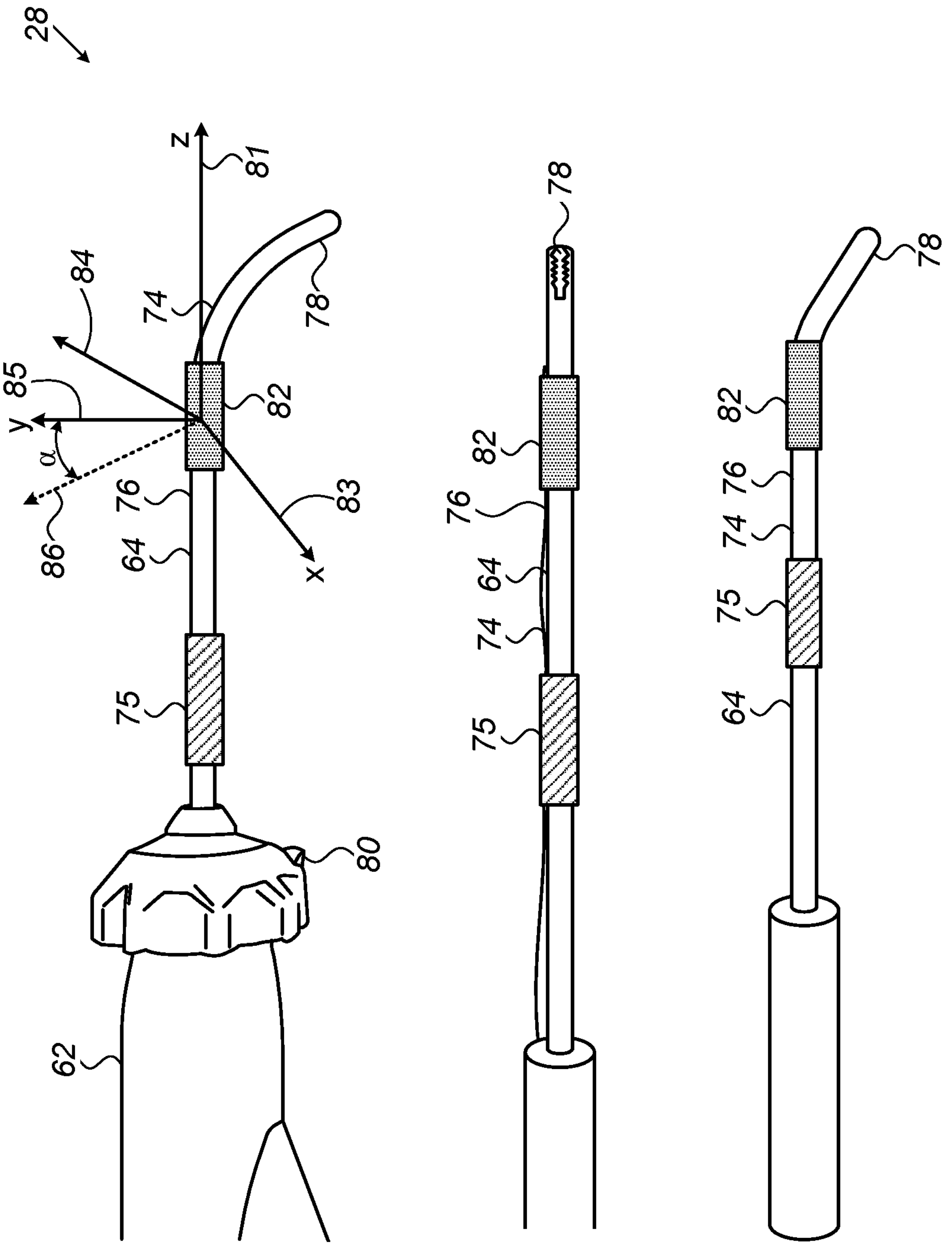
FIG. 4 is a schematic view of interchangeable heads of the ear-nose-throat (ENT) instrument of FIG. 2, each comprising a magnetic sensor disposed on a distal end of the head, according to an embodiment of the present invention.

FIG. 4 is a schematic view of interchangeable heads 64 of ear-nose-throat (ENT) instrument 28 of FIG. 2, each comprising a magnetic sensor 82 disposed on a distal end 76 of the head, according to an embodiment of the present invention.

Sensor 82 is typically formed as printed coils on a PCB. Among the advantages of using a PCB sensor are (a) a PCB sensor does not suffer from metal interference, (b) the PCB sensor may be placed in a very accurate orientation on the head, and (c) the PCB sensor is not a wound coil, but a standard printed coil, so that each PCB has substantially the same magnetic sensitivity. Therefore, based on the above advantages, the PCB sensor does not generally need calibration and therefore does not require a controller (e.g., an EEPROM) which is generally too bulky for disposing on the head.

As noted above, each interchangeable head 64 includes a position sensor 82 disposed thereon at the distal end 76 of the elongated shaft 74 of the interchangeable head 64. Position sensor 82 is electrically insulated from the elongated shaft 74 and the cutting element(s) 78. Wires extending from the head position sensor 82 are secured to the elongated shaft 74 by using, for example, self-adhesive tape 75.

In FIG. 4, sensor 82 of each interchangeable head 64 includes at least one coil with an axis 84 of the coil aligned with a given rotational angle $\alpha$ relative to a physical feature of distal end 76 to track the roll angle of the feature. In one shown embodiment, angle $\alpha$ is defined relative to a bent distal end laying in an y-z plane (defined by a longitudinal z-axis 81 and a lateral y-axis 85). As seen, direction 84 has a projection 86 on a lateral x-y plane, defined by an x-axis 83 and y-axis 85, with the given rotational angle $\alpha$ defined between projection 86 and the y-z plane.

In another embodiment, for example, angle $\alpha$ is defined relative to a rotational orientation of the rotationally asymmetrically placed distal opening 79 that is tracked to accurately rotate an electrical shaver to directly face target tissue.

Sensor 82 of each interchangeable head 64 may include a dual-axis sensor (for example, comprising two coils orthogonally aligned, or at least aligned non-parallel one with respect to the other) which can be used to detect a location, direction, and roll angle of interchangeable head 64. The head position sensor 82 may be printed on one or two printed circuit boards. For example, two coils may be printed on one or two printed circuit boards which are connected to the distal end 76 of the elongated shaft 74 so that each of the coils is orthogonal to the other. Printing the coils onto printed circuit boards provides a more compact and more standard sensor than using wound coils. The coils may be coated with an electrically insulating material.

At least some of the elongated shafts 74 may be disposed in a plastic biocompatible sleeve prior to inserting the elongated shaft 74 in a body part. In some embodiments, the sleeve may cover the elongated shaft 74 from the plastic proximal end 68 up to and including sensor 82.

Figure 5:
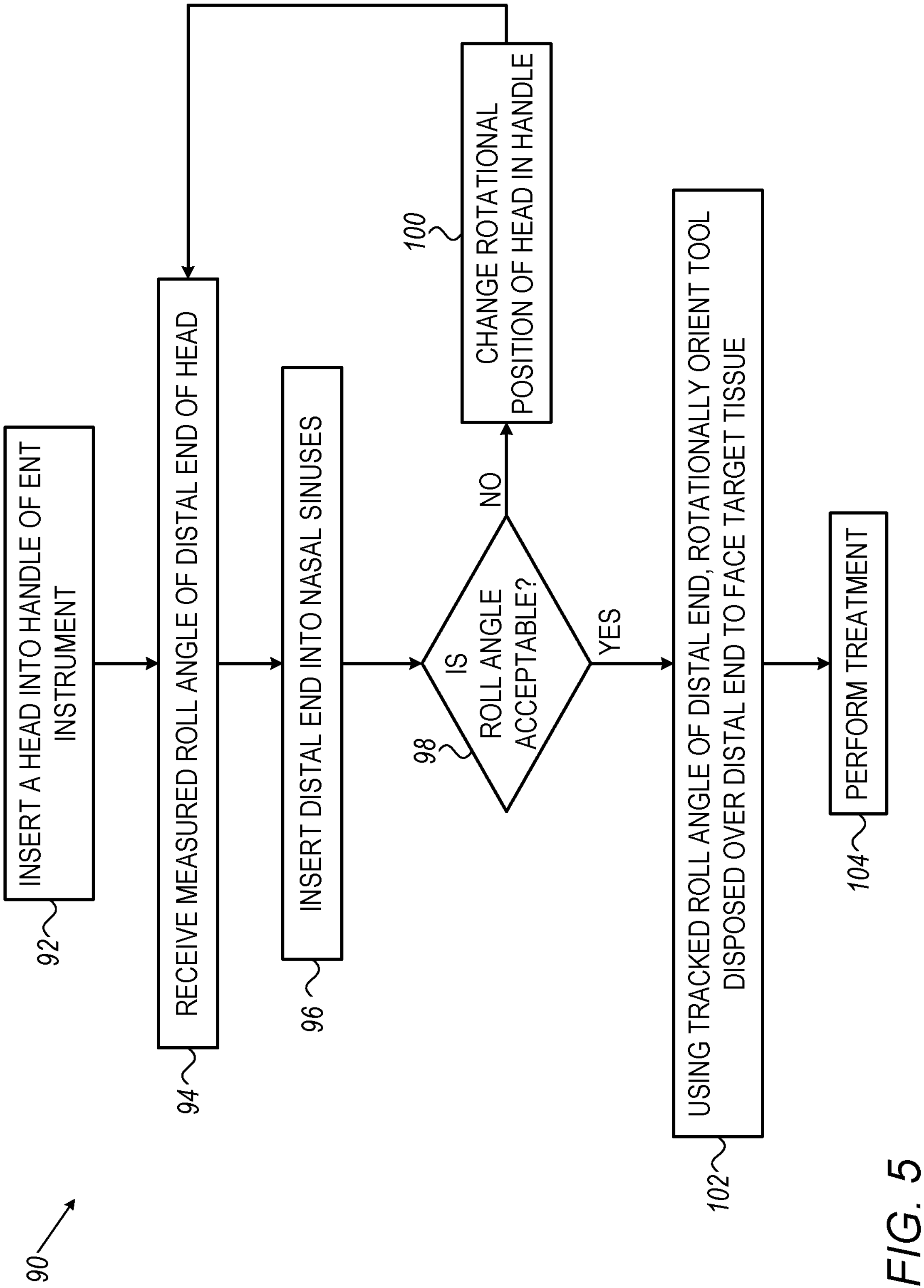
FIG. 5 is a flow chart that schematically illustrates a method and algorithm for tracking a roll angle of a head of the ear-nose-throat (ENT) instruments of FIG. 4 in a patient head, according to an embodiment of the present invention.

FIG. 5 is a flow chart 90 that schematically illustrates a method and algorithm for tracking a roll angle of a head 64 of ear-nose-throat (ENT) instrument 28 of FIG. 4 in a patient head, according to an embodiment of the present invention. The process begins with physician 54 inserting one of the interchangeable heads 64 into instrument 62, at a head insertion step 92.

As physician 54 brings the distal end of ENT instrument 28 into region 30 where alternating magnetic fields are present, processor 38 starts tracking at least a roll angle of the distal end 76 of ENT instrument 28, using signals generated by sensor 82, at a tracking step 94. The sensed roll angle may be accurate to a given tolerance, such as roll angle accuracy of up to 5 or 10%.

At an insertion step 96, physician 54 inserts the head of the instrument into the nasal sinuses with distal end 76 at a some initially preferred roll angle.

At a decision step 98, the processor 38 renders a question to the display 56 asking physician 54 whether the roll angle in which distal end is rotationally aligned is acceptable. Physician 54 provides a response via the operating controls 51 for receipt by processor 38. If the physician responds negatively, the physician rotates (block 100) the inserted interchangeable head 64 to a new rotational position and the method returns to step 94. When the interchangeable head 64 may be rotated freely with respect to handle 62, the physician may continuously rotate the inserted interchangeable head 64 while assessing if the roll angle of head 64 (e.g., of distal end 76) is acceptable, until the rotation angle is approved.

Next, the physician further maneuvers (e.g., rotationally orients) a tool disposed over the distal end so that the tool is correctly oriented relative to target tissue in the nasal sinuses, using the tracked roll angle of the tool, at a tool maneuvering step 102.

Finally, at a treatment step 104, the physician, having successfully aligned the tool, e.g., to face target tissue, performs the required treatment, such as shaving tissue.

Various features of the disclosed solution which are, for clarity, described in the context of separate embodiments may also be provided in combination in a single embodiment. Conversely, various features of the solution which are, for brevity, described in the context of a single embodiment may also be provided separately or in any suitable sub-combination.

The embodiments described above are cited by way of example, and the present invention is not limited by what has been particularly shown and described hereinabove. Rather, the scope of the invention includes both combinations and sub-combinations of the various features described hereinabove, as well as variations and modifications thereof which would occur to persons skilled in the art upon reading the foregoing description and which are not disclosed in the prior art.

The invention claimed is:

1. A system, comprising:

(a) a medical instrument comprising a handle and a head, the head being configured for insertion into an anatomical passageway of a patient and having a feature that is rotationally-asymmetric about a longitudinal axis of the medical instrument, the head of the medical instrument comprising an elongate shaft having a distal end with a bend;

(b) a position sensor, which is disposed exteriorly to an external surface of the head and is configured to generate signals in response to an externally-applied magnetic field, the position sensor being located on a section of the distal end that is proximal relative to the bend such that the position sensor is located on a portion of the head that is coaxial with the longitudinal axis of the medical instrument;

(c) a securing tape disposed exteriorly to an external surface of the head and located proximal to the position sensor, the securing tape being configured to secure a position sensor wire extending proximally from the position sensor to the elongate shaft of the head; and (d) a processor configured to:

(i) receive the signals generated by the position sensor on the head, and (ii) estimate, based on the received signals, a roll angle of the rotationally-asymmetric feature of the head about the longitudinal axis of the medical instrument.

2. The system according to claim 1, wherein the position sensor comprises at least a coil having an axis oriented at a given rotational angle relative to the rotationally-asymmetric feature of the head.

3. The system according to claim 1, wherein the rotationally-asymmetric feature comprises a medical tool.

4. The system according to claim 3, wherein the rotationally-asymmetric feature comprises an opening of the medical tool.

5. The system according to claim 3, wherein the medical tool is bent with respect to the longitudinal axis.

6. The system according to claim 1, wherein the medical tool comprises an ear, nose and throat (ENT) shaver.

7. The system according to claim 1, wherein the medical tool comprises an ENT suction tool.

8. The system according to claim 1, wherein the medical tool comprises an ENT microbrider.

9. The system according to claim 1, wherein the position sensor is a single axis sensor (SAS) printed on a circuit board.

10. The system according to claim 1, wherein the position sensor is a dual axis sensor (DAS) printed on a circuit board.

11. The system according to claim 1, further comprising a location pad, which comprises at least one magnetic field radiator configured to transmit the magnetic fields in a vicinity of the anatomical passageway.

12. The system according to claim 1, further comprising a display, wherein the processor is configured to:

(a) track a location of the head responsively to the received signals; and (b) render to the display an image including a representation of at least part of the anatomical passageway and a representation of at least part of the head in the body.

13. A system, comprising:

(a) a medical instrument comprising a handle and a head, the head comprising a bend, the head being configured for insertion into an anatomical passageway of a patient and having a feature that is rotationally-asymmetric about a longitudinal axis of the medical instrument and is located distally past the bend;

(b) a position sensor assembly comprising a position sensor, wherein the position sensor is disposed outwardly to an external surface of the head and is configured to generate signals in response to an externally-applied magnetic field, the position sensor being located proximally to the bend such that a position of the head associated with the position sensor extends coaxially with the longitudinal axis;

(c) a self-adhesive tape disposed on the external surface of the head, the self-adhesive tape being configured to secure a position wire extending proximally from the position sensor onto the head of the medical instrument, and (d) a processor configured to:

(i) receive the signals generated by the position sensor on the head, and (ii) estimate, based on the received signals, a roll angle of the rotationally-asymmetric feature of the head about the longitudinal axis of the medical instrument.

14. The system of claim 13, wherein the medical instrument further comprises a rotating cog configured to rotate the head relative to the handle.

15. The system of claim 14, wherein the rotating cog is rotatably coupled to the handle.

16. The system of 13, wherein the medical instrument further comprises a tube extending proximally from the handle.

17. The system of claim 13, wherein the head comprises a bent distal end.

18. The system of claim 17, wherein the position sensor is located proximally relative to the bent distal end.

19. A system, comprising:

(a) a medical instrument comprising a handle and a head, the head comprising an elongate shaft having a distal bend, the head being configured for insertion into an anatomical passageway of a patient and having a feature associated with the distal bend that is rotationally-asymmetric about a longitudinal axis of the medical instrument;

(b) a position sensor printed on a circuit board and is disposed externally relative to an outer surface of the head such that the position sensor is configured for insertion along with the head into an anatomical passageway of the patient, the position sensor being located proximally relative to the distal bend such that a section of the head associated with the position sensor extends coaxially with the longitudinal axis, the position sensor being configured to generate signals in response to an externally-applied magnetic field;

(c) a piece of self-adhesive material disposed externally relative to an outer surface of the head, the piece of self-adhesive material being located proximally relative to the position sensor, the piece of self-adhesive material being configured to attach a position sensor wire that is operatively coupled to the position sensor onto the elongate shaft; and (d) a processor configured to:

(i) receive the signals generated by the position sensor on the head; and (ii) estimate, based on the received signals, a roll angle of the rotationally-asymmetric feature of the head about the longitudinal axis of the medical instrument.

* * * * *